United States Patent
Broussard et al.

(10) Patent No.: US 7,084,212 B2
(45) Date of Patent: Aug. 1, 2006

(54) VULCANIZATION ACCELERATORS

(75) Inventors: Fabio Broussard, Brusaporto (IT);
Mauro Adovasio, Bergamo (IT);
Corrado Callierotti, Seriate (IT);
Gianbattista Taroni, Mozzo (IT); Jose Roncalli, Bergamo (IT)

(73) Assignee: Great Lakes Chemical Italia S.r.l., Milan (IT)

( * ) Notice: Subject to any disclaimer, the term of this patent is extended or adjusted under 35 U.S.C. 154(b) by 23 days.

(21) Appl. No.: 10/729,910

(22) Filed: Dec. 9, 2003

(65) Prior Publication Data
US 2004/0122181 A1 Jun. 24, 2004

Related U.S. Application Data

(60) Continuation of application No. 08/447,807, filed on May 23, 1995, now abandoned, which is a division of application No. 08/272,826, filed on Jul. 11, 1994, now Pat. No. 5,486,613.

(30) Foreign Application Priority Data
Jul. 15, 1993 (IT) .............................. MI93A1566
Apr. 7, 1994 (IT) .............................. MI94A0650

(51) Int. Cl.
*C08C 19/22* (2006.01)
(52) U.S. Cl. ............... 525/374; 525/326.1; 525/375; 525/347; 525/332.6; 525/329.3
(58) Field of Classification Search ............... 525/374, 525/326.1, 375, 347, 332.6, 329.3, 293
See application file for complete search history.

(56) References Cited

U.S. PATENT DOCUMENTS

| 1,780,334 | A | | 11/1930 | Burnett | 525/346 |
| 4,082,706 | A | * | 4/1978 | Danielson | 524/96 |
| 4,244,864 | A | | 1/1981 | Campbell | 546/166 |

OTHER PUBLICATIONS

Chemical Abstracts, vol. 64, No. 9, Apr. 1966, AN 12639d, Mikhant'ev, et al; "Vinylation of Quinoline Derivatives".

* cited by examiner

*Primary Examiner*—Ling-Sui Choi
(74) *Attorney, Agent, or Firm*—Oblon, Spivak, McClelland, Maier & Neustadt, P.C.

(57) ABSTRACT

The present invention relates to vulcanization accelerators constituted by compounds, derived from secondary amines, belonging to the class of enamines and to a process for their preparation.

7 Claims, 9 Drawing Sheets

VULCANIZATION ACCELERATORS

The present invention relates to vulcanization accelerators constituted by compounds belonging to the class of enamines.

More particularly, the present invention relates to vulcanization accelerators constituted by compounds, derived from secondary amines, belonging to the class of enamines and to a process for their preparation.

It is well known that the vulcanization of either natural or synthetic rubbers takes place by cross-linking between the polymeric chains, thanks to the use of sulfur or peroxides.

The vulcanization process in the presence of sulfur was optimized by means of the use of accelerators capable of reducing the vulcanization times and of securing the reproducibility of the results relating to the properties of the manufactured articles.

The known products used as vulcanization accelerators, as described, e.g., in Kirk-Othmer: "Encyclopedia of Chemical Technology", Vol. 20, pages 337–364, are many. From these, we wish to remind here aniline and its derivatives, mercaptobenzothiazole and its sulfenamides, dithiocarbamates and thiuram disulfides. In order to obtain good results, often such products are not used as individual compounds, but as combinations with each other.

Among the vulcanization accelerators a class exists of products which are defined as "secondary accelerators", useful as activators for thiazole-based primary accelerators. Examples of such products are: N,N'-diphenylguanidine (DPG), N,N'-di-orthotoluylguanidine (DOTG), 2,4,6-tris-dimethylaminomethylphenol and the condensation products of aromatic amines with aliphatic aldehydes.

The present Applicant has found now that compounds, derived from secondary amines, belonging to the class of enamines, can be used as vulcanization accelerators.

Therefore, the object of the present invention are vulcanization accelerators constituted by compounds belonging to the class of enamines, having the general formula (I):

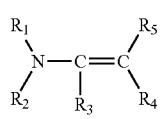

wherein:

$R_1$ and $R_2$, which are the same, or can be different from each other, represent an either linear or branched-chain $C_1$–$C_{18}$ alkyl radical; a $C_2$–$C_{18}$ alkenyl radical; a $C_3$–$C_8$ cycloalkyl radical; a $C_6$–$C_{18}$ aryl radical; a $C_7$–$C_{20}$ alkylaryl or arylalkyl radical; or $R_1$ and $R_2$, taken jointly and together with the nitrogen atom, represent a $C_3$–$C_8$ heterocyclic radical, possibly containing a second heteroatom selected from O, S and N;

$R_3$ and $R_4$, which are the same, or can be different from each other, represent a hydrogen atom; an either linear or branched-chain $C_1$–$C_{18}$ alkyl radical; a $C_2$–$C_{18}$ alkenyl radical; a $C_6$–$C_{18}$ aryl radical; a $C_7$–$C_{20}$ alkylaryl or arylalkyl radical; or $R_3$ and $R_4$, taken jointly and together with the C=C double bond to which they are bonded, represent a $C_3$–$C_{12}$ cycloalkenyl radical;

$R_5$ represents a hydrogen atom; an either linear or branched-chain $C_1$–$C_{18}$ alkyl radical; a $C_2$–$C_{18}$ alkenyl radical; or in the case when $R_3$ represents a hydrogen atom, an either linear or branched $C_1$–$C_{18}$ alkyl radical, a $C_2$–$C_{18}$ alkenyl radical, a $C_6$–$C_{18}$ aryl radical or a $C_7$–$C_{20}$ alkylaryl or arylalkyl radical; $R_4$ and $R_5$, taken jointly and together with the carbon atom bearing the C=C double bond, represent a $C_3$–$C_{12}$ cycloalkylenic radical.

Examples of $R_1$ and $R_2$ radicals are methyl, ethyl, propyl, pentyl, hexyl, heptyl, ethylhexyl, butyl, octyl, phenyl, and so forth.

Examples of $C_3$–$C_8$ heterocyclic radicals, in the case when $R_1$ and $R_2$ are taken jointly and together with the nitrogen atom, are morpholine, pyrrolidine, piperidine, piperazine, thiomorpholine, thiazolidine, benzothiazolidine, and so forth.

Examples of $R_3$ and $R_4$ radicals are methyl, ethyl, propyl, butyl, phenyl, and so forth.

Examples of $C_3$–$C_{12}$ cycloalkenyl radicals, in the case when $R_3$ and $R_4$ are taken jointly and together with the C=C double bond to which they are bonded, are cyclopentene, cyclohexene, cycloheptene, cyclooctene, cyclododecene and so forth.

Examples of $R_5$ radicals are methyl, ethyl, propyl, butyl, hexyl, heptyl, and so forth.

Examples of $C_3$–$C_{12}$ cycloalkylenic radicals, in the case when $R_4$ and $R_5$ are taken jointly and together with the carbon atom bearing the C=C double bond, are cyclohexylidene, cyclooctylidene, and so forth.

The capability shown by the compounds having general formula (I), of acting as vulcanization accelerators was evidenced by means of the rheometric curves reported in FIGS. 1–3 and 8 (in which time is reported on the abscissa; torque is reported on the ordinate; the meanings of the characters reported on the rheometric curves will be specified hereinafter), obtained by measuring the stress applied to an oscillating disk embedded inside a rubber sample during the vulcanization. The rheometric curves were determined by using Monsanto's Rheometer 100.

The rheometric curves obtained from samples of natural rubber admixed with the compounds having the general formula (I), as disclosed above, indicate that these compounds are vulcanization accelerators. In fact, when they are used as the only vulcanization accelerators, the rheometric curves reported in FIG. 1 indicate that the vulcanization, which otherwise would take place only after some hours, takes place during a short period of minutes.

The compounds having the general formula (I) can also be used in combination with other vulcanization accelerators such as, e.g., mercapto-benzothiazole sulfenamides.

Figure 2:
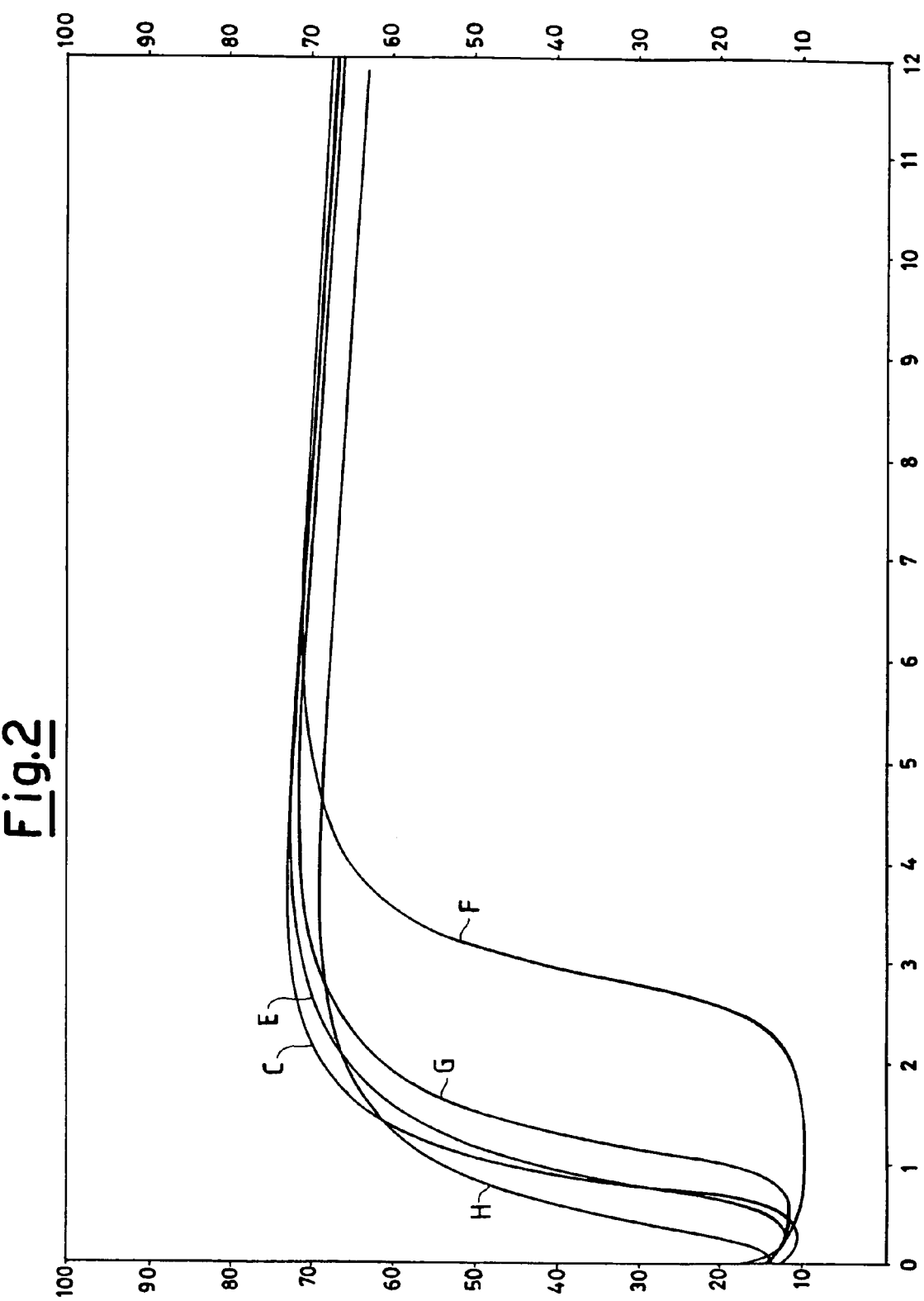
FIGS. 2, 3 and 8 are rheometric curves that illustrate the accelerators of compounds having the general formula (I).
Figure 3:
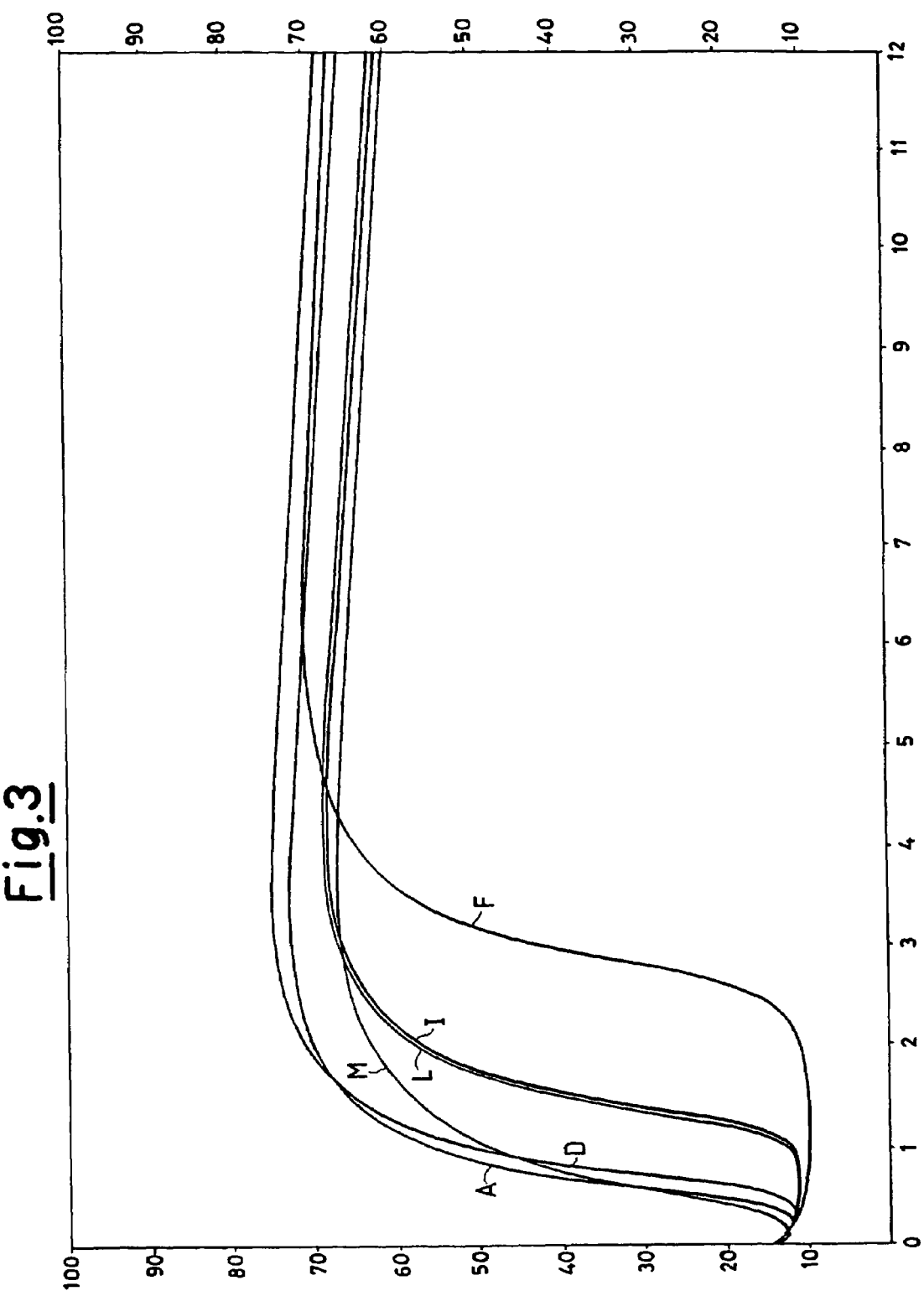
Figure 8:
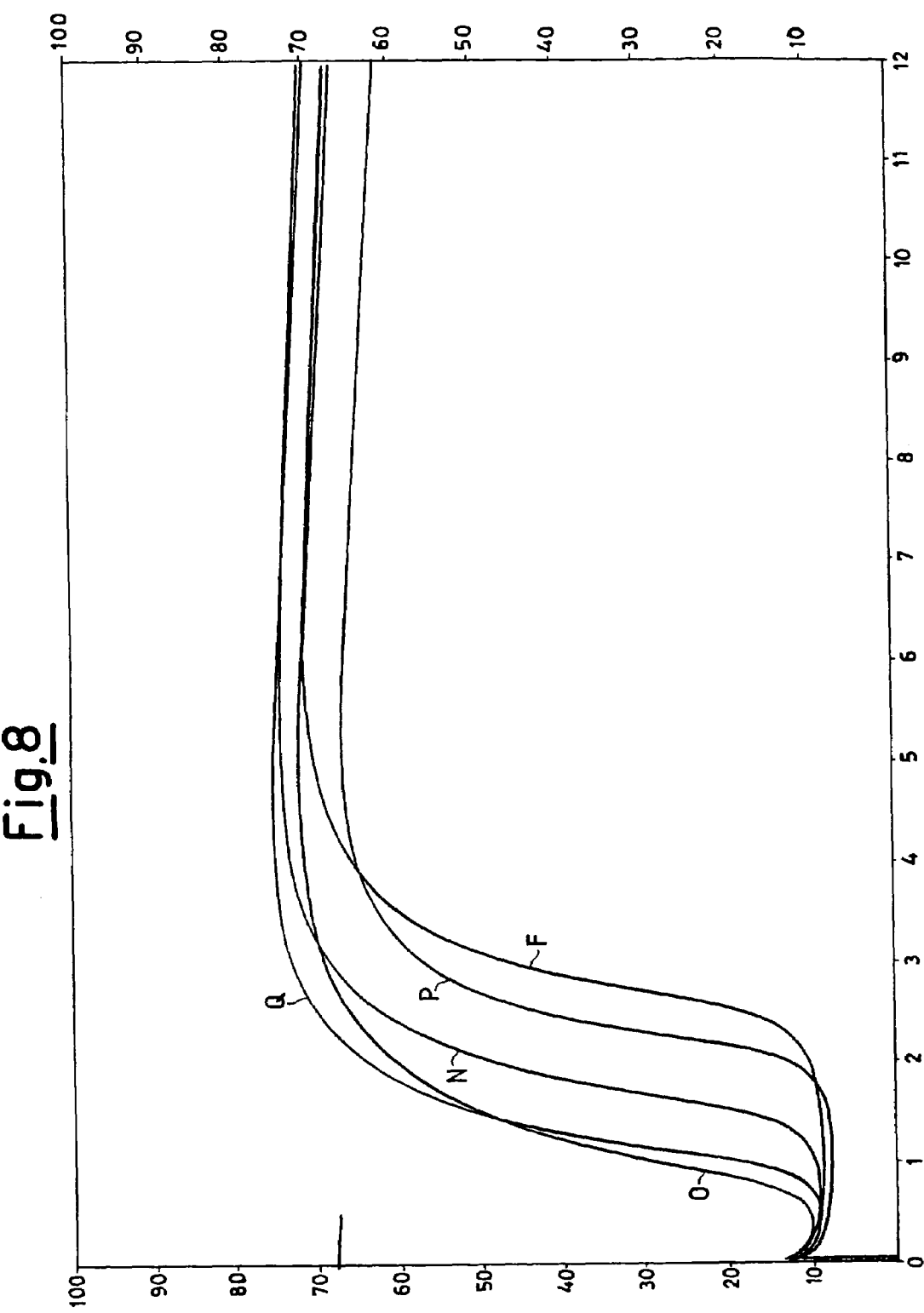

In FIGS. 2, 3 and 8, the rheometric curves are reported which were obtained by using N-cyclohexyl-2-mercaptobenzothiazole sulfenamide (CBS) either alone, or together with a compound having the general formula (I). Such curves indicate that, when CBS is used in combination with a compound having the general formula (I), the necessary time to reach 90% of the maximal peak value of the vulcanization curve $t_c(90)$ becomes considerably shorter, thus allowing a faster vulcanization kinetics to be achieved than as allowed CBS alone.

A process for synthetizing the compounds having the general formula (I) disclosed hereinabove, comprises the reaction of 1 mol of a secondary amine having the general formula (II):

$$HNR_1R_2 \quad (II)$$

in which $R_1$ and $R_2$ have the same meaning as disclosed above, with 0.5 mol of an aliphatic or an alicyclic aldehyde or of an open or cyclic ketone, having at least 1 hydrogen atom in the alpha-position to the aldehydic or ketonic carbonyl group, so as to secure the formation of the C═C double bond in the resulting compound having the general formula (I).

Said reaction takes place in the presence of a catalyst such as, e.g., potassium carbonate, at temperatures comprised within the range of from 20° C. to 120 C, preferably of from 60° C. to 80° C., under the atmospheric pressure and during a time of from 0.5 to 8 hours, preferably of from 1 to 3 hours.

When the reaction is complete, the resulting reaction mixture is cooled down to room temperature, an inert organic solvent such as, e.g., n-pentane, cyclohexane, is added and the solid phase, containing water-impregnated potassium carbonate, is filtered off from the organic phase containing the compound having the general formula (I).

The so obtained organic phase is purified by fractional distillation under vacuum, at a pressure comprised within the range of from 0.5 mmHg to 50 mmHg and at a temperature comprised within the range of from 40° C. to 200° C.

The process for synthetizing compounds having the general formula (I) is anyway described in published papers, such as, i.e., in Houben-Weil (1957), Vol. 11/1, pages 171-foll.

Secondary amines having the general formula (II) useful for the purpose of the present invention are morpholine, piperidine, pyrrolidine, dimethylamine, dipropylamine, diethylamine, dibutylamine, diisopropylamine, dibenzylamine, dicyclohexylamine, N-alkyl-aryl amines, piperazine, diallylamine, thiazolidine, thiomorpholine, and so forth.

Aliphatic or alicyclic aldehydes useful for the purpose of the present invention are butyraldehyde, n-hexaldehyde, n-heptaldehyde, n-octaldehyde, cyclohexanecarboxyaldehyde, cyclooctylaldehyde, and so forth.

Open or cyclic ketones useful for the purpose of the present invention are cyclopentanone, cyclohexanone, methyl-ethyl-ketone, methyl-butyl-ketone, butyrophenone, and so forth.

Also compounds having the general formula (I) available from the market, manufactured by Aldrich, were submitted to technological evaluation.

The enaminic function of the compounds having the general formula (I) synthetized by means of the process disclosed hereinabove, is confirmed by the analysis carried out by FT-IR spectroscopy (obtained by using a NICOLET MAGNA IR 550 spectrophotometer) reported in FIGS. 4 and 5 (in which on the abscissa and on the ordinate, the wavelength as $cm^{-1}$ and the transmittance as % are reported, respectively), carried out on high-purity samples (GC>95% confirmed by gas chromatography), in which a sharp absorption band inequivocally appears at a wavelength of round 3045 $cm^{-1}$ and 1655 $cm^{-1}$, which is also present in the products available from the market.

Figure 4:
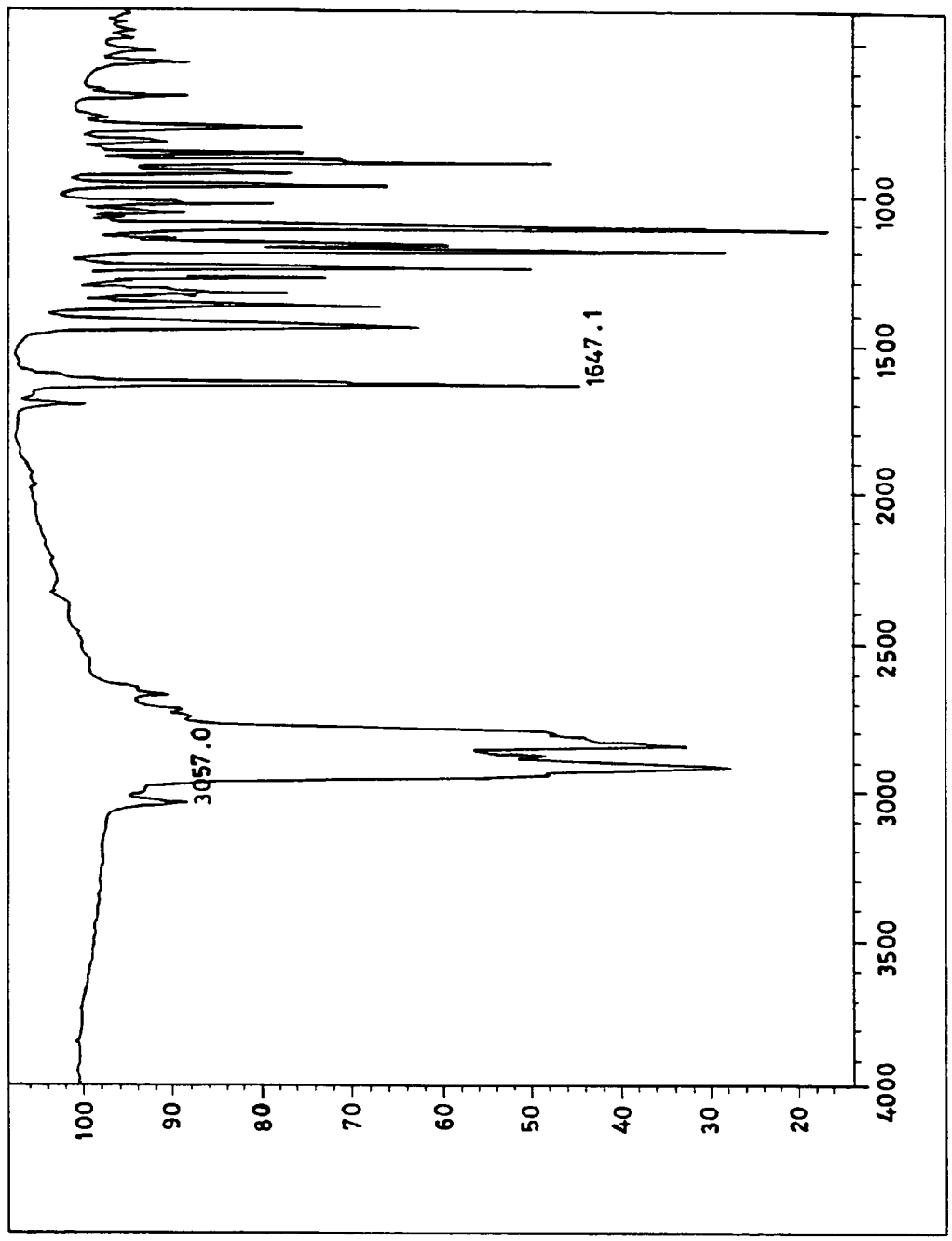
In FIG. 4, the FT-IR spectra of 1-morpholino-1-cyclohexene, manufactured by Aldrich, is reported.

In FIG. 4, the FT-IR spectra of 1-morpholino-1-cyclohexene, manufactured by Aldrich, is reported.

Figure 5:
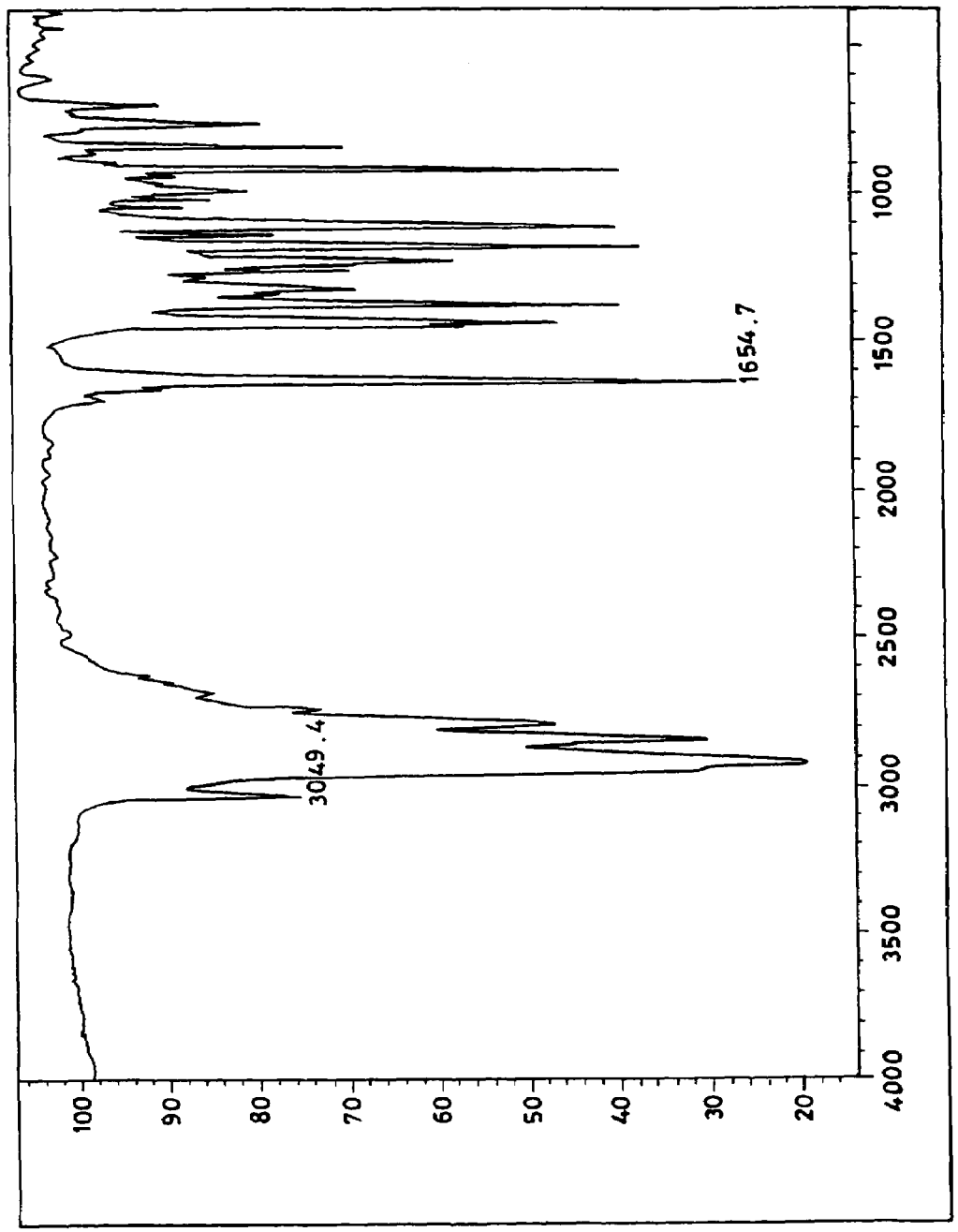
In FIG. 5, the FT-IR spectra of N-n-octene-($\Delta^1$)-yl-piperidine is reported (corresponding to compound No. 2 of the present invention, reported in the following in the examples).

In FIG. 5, the FT-IR spectra is reported of N-n-octene-($\Delta^1$)-yl-piperidine (corresponding to compound No. 2 of the present invention, reported in the following in the examples).

The present Applicant was also able to isolate, from the products deriving from the condensation of an aromatic amine with an aliphatic aldehyde, a novel compound belonging to the class of enamines, as an active substance useful as a vulcanization accelerator.

Therefore, a novel compound falls within the purpose of the present invention, and hence is a further object thereof, which belongs to the class of enamines, and has the formula (III):

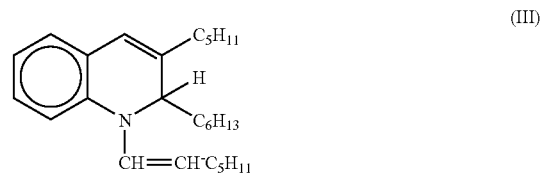

and is useful as a vulcanization accelerator.

Figure 6:
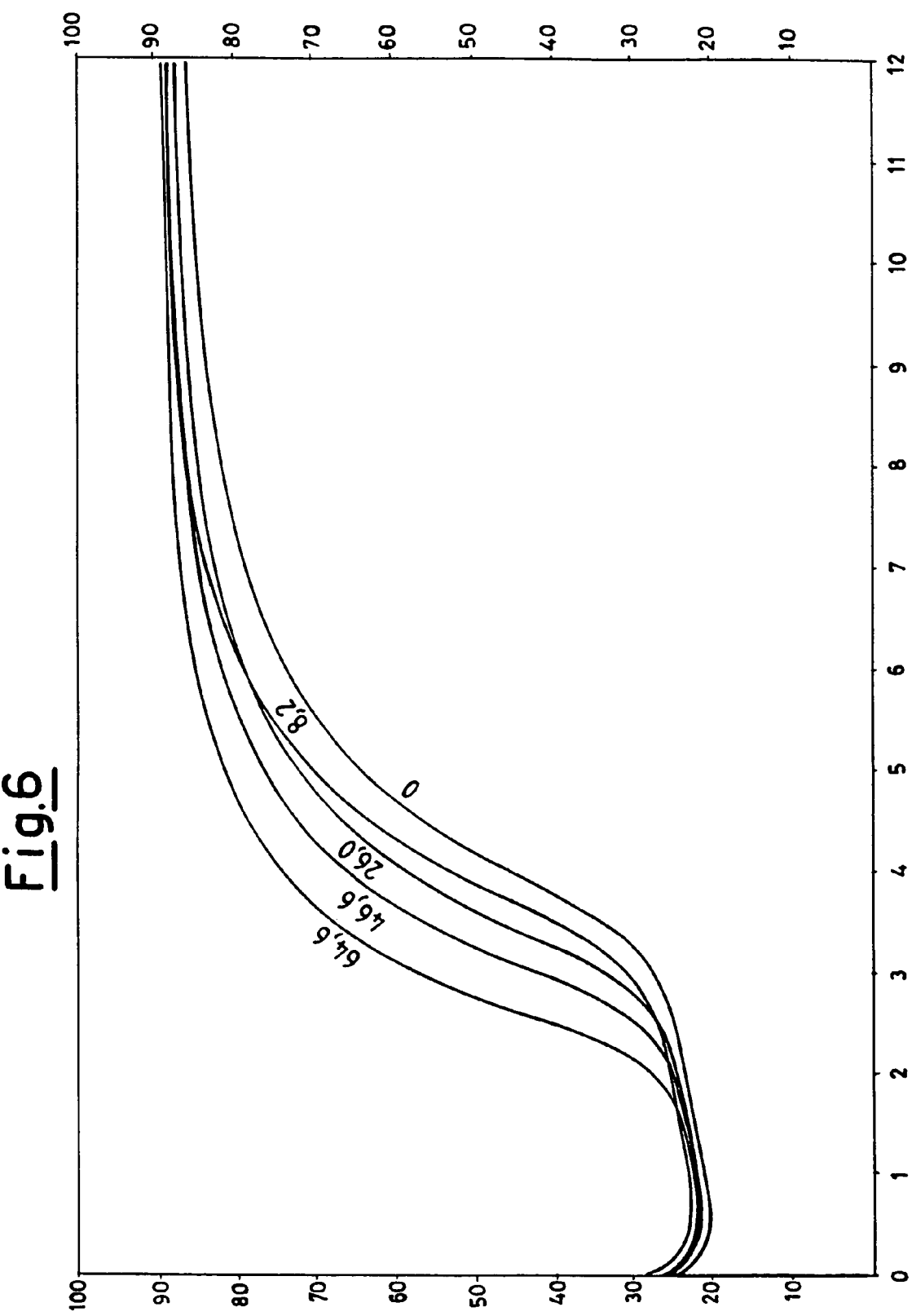
FIG. 6 is a rheometric curve that illustrates that compounds having general formula (III) are capable of acting as vulcanization accelerators.

The capability of acting as vulcanization accelerator displayed by the compound of formula (III) was evidenced by means of the rheometric curves reported in FIG. 6 (in which on the abscissa the time, and on the ordinate the torque is reported), obtained by measuring the stress applied to an oscillating disk embedded inside a rubber sample during the vulcanization (ASTM D3185-75). The curves have been determined by using Monsanto's Rheometer 100.

The rheometric curves obtained from samples of styrene-butadiene rubber (SBR) admixed with distillation fractions of the products deriving from the condensation of the aromatic amine with the aliphatic aldehyde, containing variable amounts of the compound of formula (III) which constitutes a further object of the present invention, indicate that the necessary time for reaching 90% of maximal peak valu of the cross-linking curve $t_c(90)$ is the shorter, the higher the percent content of compound of formula (III) contained in the formulation.

Figure 7:
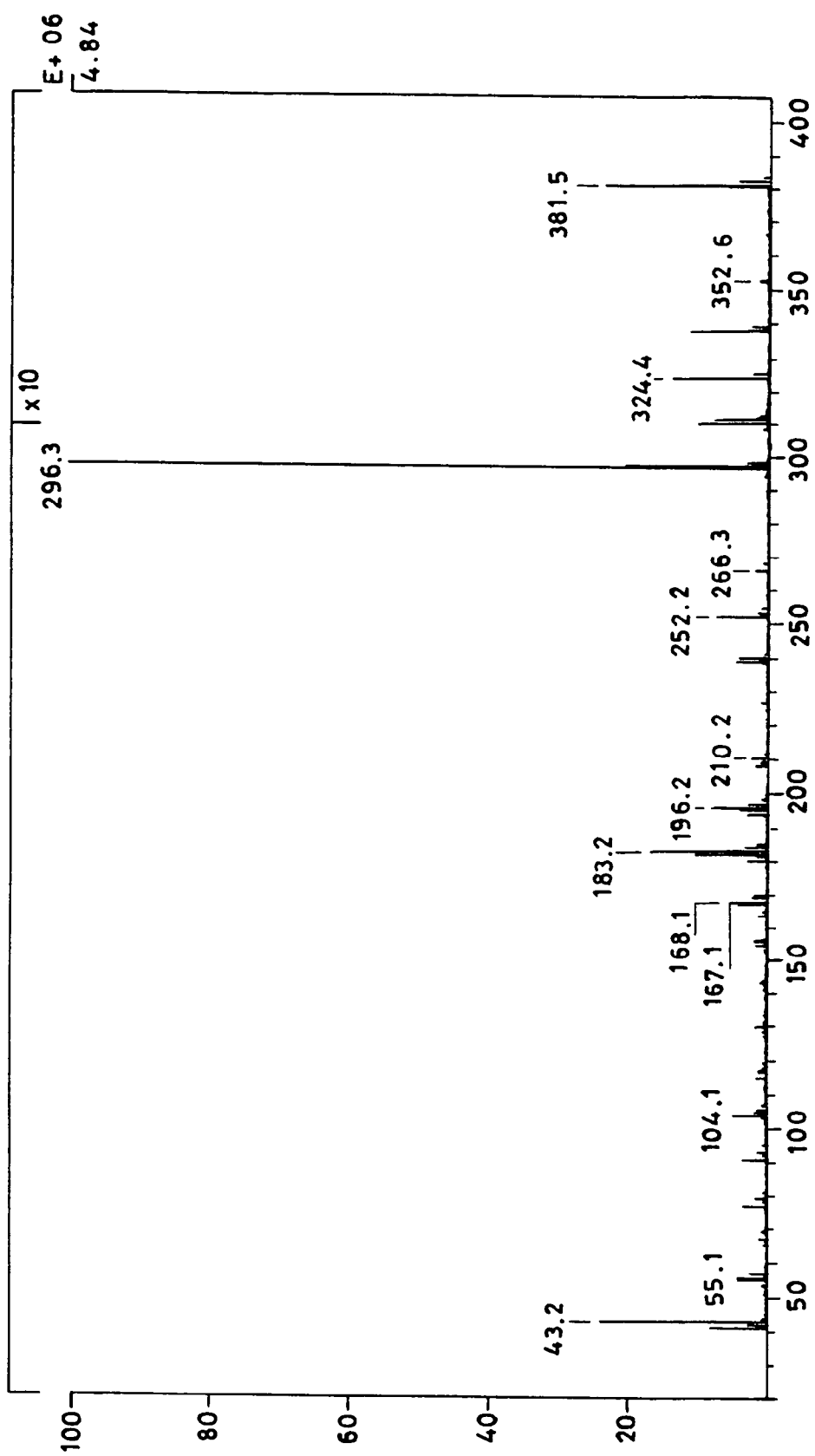
FIG. 7 is a GC/MC spectra of a compound of formula III.

The compound of formula (III) was furthermore characterized by means of the interpretation of the fragmentation observed through gas chromatography/mass spectrometry (GC/MS) techniques. FIG. 7 displays the mass spectra of said compound, as determined by operating under the following conditions:

Triple quadrupole Finnigan mass spectrometer Model TSQ 700 interfaced to a Varian 3400 gas chromatograph.
Fused silica T.A.P. (Triglyceride Analysis Phase) 50% phenyl/50% methyl-polysiloxane, 5 m long capillary column of 0.25 mm of inner diameter and 0.1 μm thick film (ex Crompack).
Oven temperature schedule: from 45° C. up to 300° C., with a temperature increase rate of 15° C./min; end isotherm 10 min.
Carrier gas: helium at 1.5 ml/min.
Injection system:
(a) SPI injector Varian Model 1093; initial temperature 42° C., end temperature 250° C., temperature increase rate 180° C./min;
(b) split injector; temperature 250° C., splitting ratio 30:1.
Splitless injection;
Injected volume: 1.0 μl;
Sample concentration: 1.0 mg/ml in $CH_2Cl_2$;
Transfer line temperature: 280° C.;

Source temperature: 150° C.;
Ionization system:
(a) EI: electron energy 70 eV, emission current 200 μA;
(b) CI: electron energy 100 eV, emission current 200 μA, reagent gas isobutane at 0.5 torr.
Analyzer quadrupole scanning: from m/z 33 to m/z 750 within 1.0 s in EI; from m/z 118 to m/z 750 within 1.0 s in CI.
Electromultiplier voltage: 1000 V.

A process for synthetizing the compound of formula (III) disclosed above comprises:
(a) causing two mols of heptaldehyde:

to react in the presence of a 37% hydrochloric acid solution;
(b) causing the crotonaldehyde obtained from the (a) step:

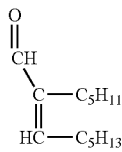

and any unreacted heptaldehyde from above (a) step to react with 1 mol of aniline:

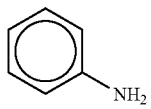

with a mixture being thus obtained, which consists of the compounds having the formulae (III) (reported above), (IV), (V) and (VI):

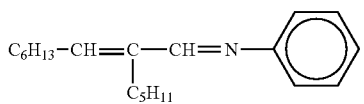
(IV)

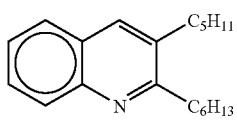
(V)

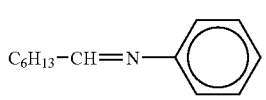
(VI)

(c) separating the mixture of compounds obtained from the above (b) step, by distillation.

The reaction of the (a) step is carried out at a temperature comprised within the range of from 90° C. to 150° C., under atmospheric pressure. The reaction is carried out in the presence of an organic solvent, preferably a hydrocarbon, in particular xylene or toluene. During a reaction time comprised within the range of from 0.5 to 8 hours, by means of an azeotropic distillation apparatus, acidic water (containing HCl) is separated which partially derives from the reaction and partially from the solution of hydrochloric acid, and the organic solvent is recycled.

The reaction of the (b) step is carried out at a temperature comprised within the range of from 120° C. to 170° C., under the atmospheric pressure. During the addition of aniline, which takes place during a time comprised within the range of from 1 to 6 hours, further acidic water is azeotropically distilled off; the resulting mixture is kept at a temperature comprised within the range of from 160° C. to 170° C. during a time comprised within the range of from 1 to 3 hours.

In the (c) step, to the mixture obtained from the (b) step of the above process, cooled down at a temperature comprised within the range of from 70° C. to 90° C., a basic substance (sodium hydroxide, or the like) and water are added, so as to neutralize the acidity. The aqueous phase is then separated from the organic phase, which is washed in water.

The organic phase is distilled at a temperature comprised within the range of from 100° C. to 200° C., initially under the atmospheric pressure in order to distil the solvent off, then under a residual pressure comprised within the range of from 10 mmHg to 20 mmHg in order to remove any unreacted aniline.

The resulting residue, which contains 40%–50% of compound of formula (III), is submitted to a further distillation under vacuum, under a pressure comprised within the range of from 0.1 mmHg to 1.0 mmHg, and at a temperature comprised within the range of from 180° C. to 250° C.

The central fraction obtained from the above disclosed distillation contains 75%–85% of compound of formula (III).

The vulcanization accelerators having the general formula (I) can be used in either natural or synthetic rubbers or such as, e.g., SBR, NBR, BR, EPDM, and so forth. The same holds true for th compound of formula (III), which can be used as a vulcanization accelerator in natural, as well as synthetic, rubbers, such as, e.g., SBR, NBR, BR, EPDM, and so forth.

In order to better understand the present invention and to practice it, some illustrative examples are reported in the following, which in no way should be regarded as being limitative of the purview of the same invention.

EXAMPLE 1

Preparation of N-n-hexen-($\Delta^1$)-yl piperidine
(Compound No. 1)

85.15 g (1 mol) of piperidine and 25.23 g (0.182 mol) of anhydrous potassium carbonate are charged to a reactor of 1 litre of capacity equipped with mechanical stirring meanings, thermometer, addition funnel and reflux condenser.

The resulting suspension is heated up to 80° C. and is kept at that temperature with stirring, for 15 minutes. 50.08 g (0.5 mol) of n-hexaldehyde is then added in a regular and continuous way during 20 minutes.

When the addition is complete, the resulting mixture has a milky appearance due to water release which binds with potassium carbonate. The above mixture is kept with stirring at 80° C. for 3 hours and is then cooled down to room temperature.

150 g of n-pentane is added, the mixture is filtered in order to remove the water impregnated catalyst (solid phase) and the resulting organic phase is submitted to fractional distillation.

Said distillation is carried out in a still constituted by a kettle of 500 ml of capacity equipped with thermometer, stirrer, column, condenser and device for fraction collection.

After recovering the solvent and amine excess, a fraction of 71 g of distilled product, corresponding to compound No. 1 is collected by operating under the following conditions:

head temperature: 70° C.–79° C.;
kettle temperature: 72° C.–84° C.;
vacuum: 0.8 mmHg.

The so obtained compound No. 1 is analyzed by gas chromatography (GC) and resulted to be 99.2% pure, in a yield of 84.9% based on charged carbonyl compound (hexaldehyde).

Compound No. 1 is characterized by FT-IR. The obtained spectra clearly shows the typical absorption bands of enamines at 3047.5 cm$^{-1}$ and 1654.1 cm$^{-1}$, corresponding to vibrations of enaminic type double bond stretching.

The other compounds (Compounds Nos. 2–9), for which the reaction conditions and the characteristics are reported only, are prepared in an analogous way to as disclosed in Example 1.

EXAMPLE 2

Preparation of N-n-octen-($\Delta^1$)-yl piperidine (Compound No. 2)

Amine: piperidine; 85.15 g (1 mol);
Carbonylic compound: n-octaldehyde; 64.11 g (0.5 mol);
Reaction temperature: 80° C.;
Distillation temperature range: 72° C.–84° C. (head); 87° C.–92° C. (kettle); 0.5 mmHg (vacuum);
Yield based on carbonylic compound: 81.9%;
GC purity: 99.1%;
FT-IR (absorption at cm$^{-1}$): 3049.4 and 1654.7. The FT-IR spectra of compound No. 2 is reported in FIG. 5.

EXAMPLE 3

Preparation of N-n-hepten-($\Delta^1$)-yl pyrrolidine (Compound No. 3)

Amine: pyrrolidine; 71.12 g (1 mol);
Carbonylic compound: n-heptaldehyde; 57.08 g (0.5 mol);
Reaction temperature: 80° C.;
Distillation temperature range: 72° C.–81° C. (head); 76° C.–103° C. (kettle); 0.5 mmHg (vacuum);
Yield based on carbonylic compound: 73.0%;
GC purity: 98.5%;
FT-IR (absorption at cm$^{-1}$): 3045.2 and 1654.6.

EXAMPLE 4

Preparation of N-n-hepten-($\Delta^1$)-yl morpholine (Compound No. 4)

Amine: morpholine; 87.12 g (1 mol);
Carbonylic compound: n-heptaldehyde; 57.09 g (0.5 mol);
Reaction temperature: 70° C.–80° C.;
Distillation temperature range: 80° C.–82° C. (head); 87° C.–101° C. (kettle); 0.4 mmHg (vacuum);
Yield based on carbonylic compound: 68.8%;
GC purity: 98.2%;
FT-IR (absorption at cm$^{-1}$): 3048.3 and 1655.7.

EXAMPLE 5

Preparation of N-n-buten-($\Delta^1$)-yl piperidine (Compound No. 5)

Amine: piperidine; 85.15 g (1 mol);
Carbonylic compound: butyraldehyde; 36.05 g (0.5 mol);
Reaction temperature: 60° C.;
Distillation temperature range: 91° C.–93° C. (head); 96° C.–101° C. (kettle); 25 mmHg (vacuum);
Yield based on aldehyde: 60.6%;
GC purity: 99.1%;
FT-IR (absorption at cm$^{-1}$): 3049.0 and 1654.7.

EXAMPLE 6

Preparation of N-n-buten-($\Delta^1$)-yl morpholine (Compound No. 6)

Amine: morpholine; 87.12 g (1 mol);
Carbonylic compound: butyraldehyde; 36.05 g (0.5 mol);
Reaction temperature: 80° C.;
Distillation temperature range: 42° C.–48° C. (head); 65° C.–75° C. (kettle); 0.6 mmHg (vacuum);
Yield based on carbonylic compound: 67.6%;
GC purity: 99.5%;
FT-IR (absorption at cm$^{-1}$): 3049.4 and 1656.2.

EXAMPLE 7

Preparation of N-n-octen-($\Delta^1$)-yl morpholine (Compound No. 7)

Amine: morpholine; 87.12 g (1 mol);
Carbonylic compound: n-octaldehyde; 64.11 g (0.5 mol);
Reaction temperature: 80° C.;
Distillation temperature range: 97° C.–104° C. (head); 100° C.–106° C. (kettle); 0.8 mmHg (vacuum);
Yield based on carbonylic compound: 86.1%;
GC purity: >99.5%;
FT-IR (absorption at cm$^{-1}$): 3049.3 and 1655.6.

EXAMPLE 8

Preparation of N-n-hexen-($\Delta^1$)-yl morpholine (Compound No. 8)

Amine: morpholine; 87.12 g (1 mol);
Carbonylic compound: n-hexaldehyde; 50.08 g (0.5 mol);
Reaction temperature: 80° C.;
Distillation temperature range: 74° C.–78° C. (head); 78° C.–80° C. (kettle); 0.5 mmHg (vacuum);
Yield based on carbonylic compound: 87.2%;
GC purity: 99.4%;
FT-IR (absorption at cm$^{-1}$): 3048.3 and 1655.8.

EXAMPLE 9

Preparation of 1-dibutylamino-1-heptene (Compound No. 9)

Amine: 1-dibutylamine; 129.24 g (1 mol);
Carbonylic compound: n-heptaldehyde; 57.09 g (0.5 mol);
Reaction temperature: 70° C.–80° C.;
Distillation temperature range: 120° C.–125° C. (head); 130° C.–140 C. (kettle); 2 mmHg (vacuum);
Yield based on carbonylic compound: 82.3%;
GC purity: 96.8%;
FT-IR (absorption at cm$^{-1}$): 3048.4 and 1652.1.

EXAMPLE 10

Preparation of Enamine of Formula

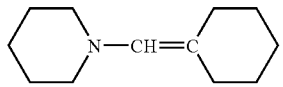

(Compound No. 10)

Amine: piperidine; 85.15 g (1 mol);
Carbonylic compound: cyclohexanecarboxyaldehyde; 56.08 g (0.5 mol);
Reaction temperature: 80° C.;
Distillation temperature range: 162° C.–165° C. (head); 165° C.–170° C. (kettle); 60 mmHg (vacuum);
Yield based on carbonylic compound: 81.3%;
GC purity: 99.2%;
FT-IR (absorption at $cm^{-1}$): 3040.8 and 1675.3.

EXAMPLE 11

Preparation of Enamine of Formula

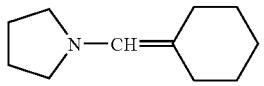

(Compound No. 11)

Amine: pyrrolidine; 71.12 g (1 mol);
Carbonylic compound: cyclohexanecarboxyaldehyde; 56.08 g (0.5 mol);
Reaction temperature: 80° C.;
Distillation temperature range: 82° C.–83° C. (head); 86° C.–100° C. (kettle); 0.4 mmHg (vacuum);
Yield based on carbonylic compound: 87.1%;
GC purity: 99.3%;
FT-IR (absorption at $cm^{-1}$): 3051.0 and 1665.6.

EXAMPLE 12

Preparation of N-methyl-N-n-hepten-($\Delta^1$)-yl aniline (Compound No. 12)

Amine: N-methylaniline; 107.16 g (1 mol);
Carbonylic compound: heptaldehyde; 57.09 g (0.5 mol);
Reaction temperature: 80° C.;
Distillation temperature range: 104° C.–114° C. (head); 122° C.–128° C. (kettle); 0.3–0.4 mmHg (vacuum);
Yield based on carbonylic compound: 60%;
GC purity: 97.2%;
FT-IR (absorption at $cm^{-1}$): 3063.6 and 1653.4.

EXAMPLE 13

Preparation of 1-phenyl-1-N-pentamethylene-ethylene (Compound No. 13)

85.15 g (1 mol) of piperidine, 100 g of toluene, 2.33 g of acetic acid (0.039 mol) and 120.15 g (1 mol) of acetophenone are charged to a reactor of 1 litre of capacity equipped with mechanical stirrer, thermometer and reflux condenser.

The resulting mixture is heated up to its reflux temperature (about 120° C.) and is kept at that temperature, with stirring, during 20 hours. Said reaction mixture is then submitted to fractional distillation.

Such a distillation is carried out on a still consisting of a kettle of 1 litre of capacity quipped with thermometer, stirring means, 20-cm-long Vigreux column, condenser and device for fraction collection.

After recovering the solvent, and any unreacted acetic acid, acetophenone and amine, a fraction of 28 g of distilled product is collected, which corresponds to compound No. 13, by operating under the following conditions:
head temperature: 175° C.–182° C.;
kettle temperature: 180° C.–200° C.;
vacuum: 58 mmHg–60 mmHg.

The Compound No. 13 obtained in that way was analyzed by gas chromatography (GC) and resulted to be 97.5% pure, a yield of about 15%, based on charged carbonylic compound (acetophenone).

The Compound No. 13 was characterized by FT-IR. The obtained spectra displays very evident absorption bands which are typical for enamines, at 3107.5 $cm^{-1}$ and 1570.0 $cm^{-1}$.

EXAMPLES 14–19

Compounds based on natural rubber were prepared, the components of which are reported in Table 1.

TABLE 1

| Components | % by weight* |
| --- | --- |
| Natural rubber SMR 10 | 100.00 |
| Zinc oxide | 5.00 |
| Stearine | 1.00 |
| High-aromatics oil | 5.00 |
| Black N 375 | 45.00 |
| Sulfur | 2.00 |
| Compound of formula (I)** or of formula (III) | 1.00 |

*% by weight, based on rubber.
**Compound of formula (I): Example 14: (A) N-n-heptene-($\Delta^1$)-yl pyrrolidine (Compound No. 3); Example 15: (B) 1-dibutylamino-1-heptene (Compound No. 9); Example 16: (C) N-n-octene-($\Delta^1$)-yl piperidine (Compound No. 2); Example 17: (D) N-n-hexene-($\Delta^1$)-yl piperidine (Compound No. 1); Example 18: (E) 1-pyrrolidino-1-cyclohexene (ex Aldrich); Example 19: (R) compound of formula (III).

Monsanto Rheometer is used under the following operating conditions:
oscillating arc: ±1°;
temperature: 160° C.

Figure 1:
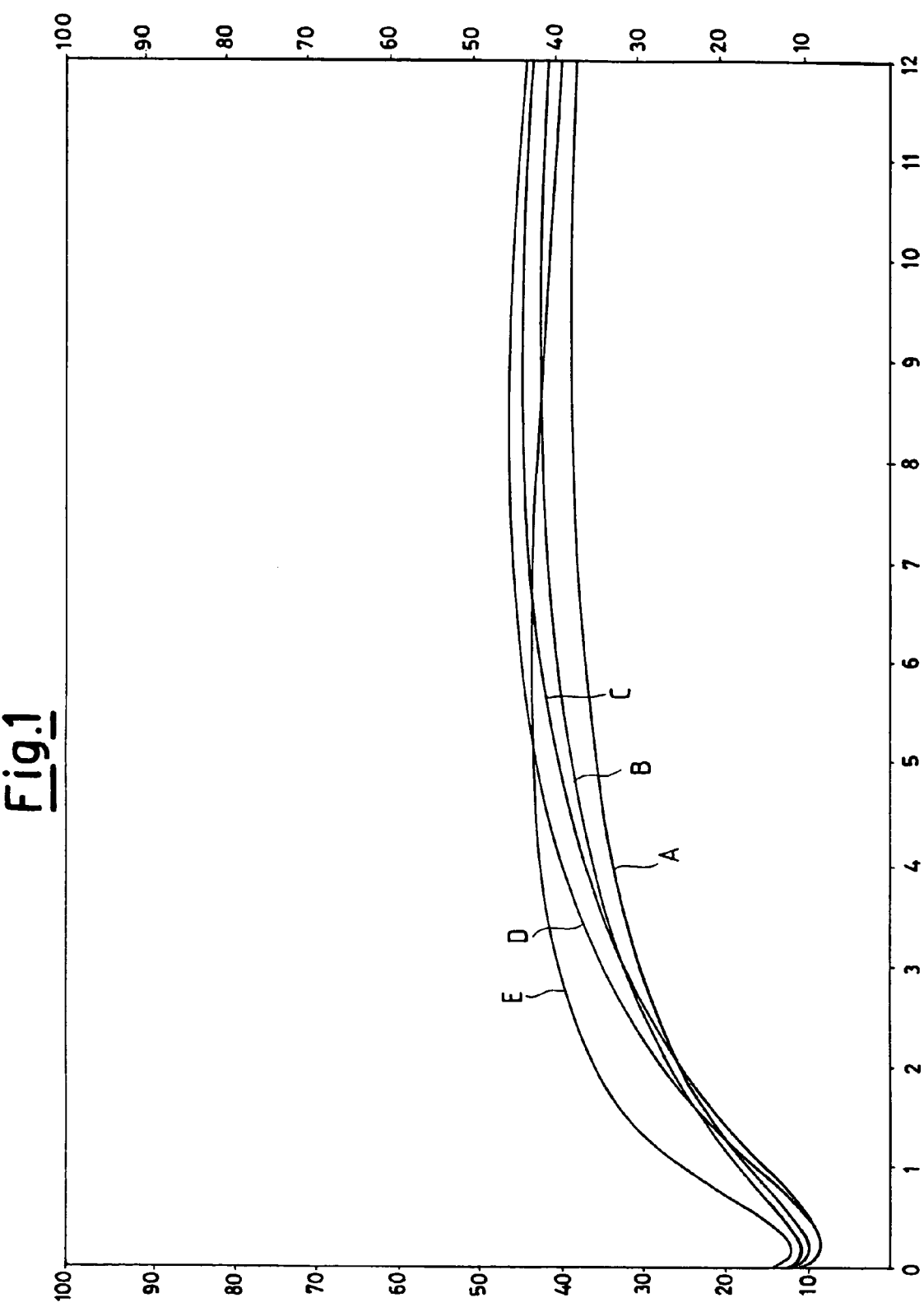
FIGS. 1 and 9 are rheometric curves that illustrate that compounds having the general formula (I) and formula (III) are vulcanization accelerators.
Figure 9:
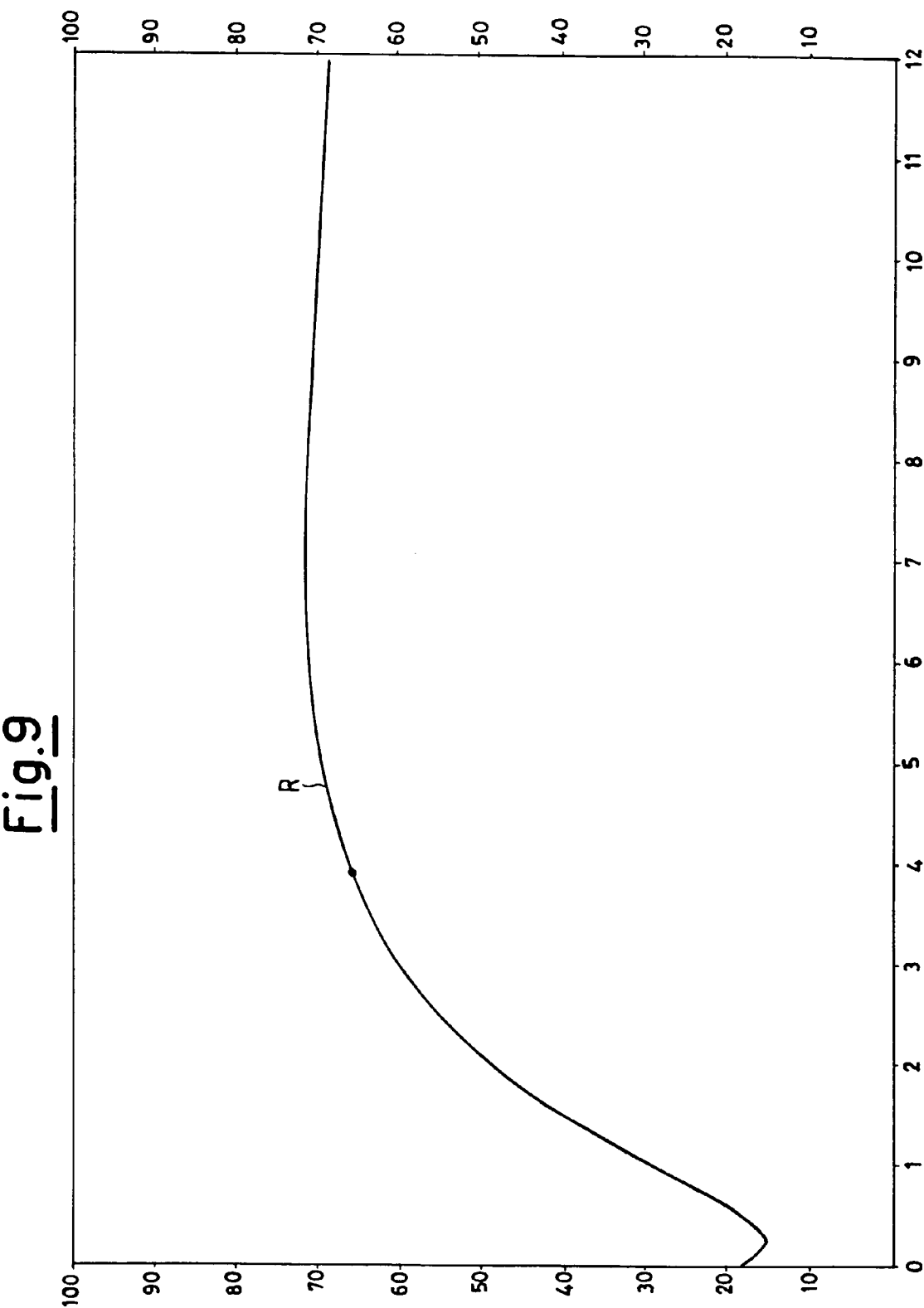

From the resulting rheometric curves, reported in FIGS. 1 and 9 (the letters reported on said rheometric curves correspond to the above reported compounds), the $t_c(90)$ values were computed, which are reported in Table 2.

The rheometric curves reported in FIG. 1 and in FIG. 9 clearly display that the compounds having the general formula (I) and formula (III), are vulcanization accelerators.

In fact, otherwise, the curves would display a flat appearance, because the vulcanization deriving from sulfur bridge formation would require som hours before reaching 90% of maximal torque.

TABLE 2

| Example No. | Compound of formula (I) | $t_c(90)$ |
|---|---|---|
| 14 | (A) | 12 min. 15 sec. |
| 15 | (B) | 12 min. 30 sec. |
| 16 | (C) | 12 min. 45 sec. |
| 17 | (D) | 12 min. 00 sec. |
| 18 | (E) | 7 min. 30 sec. |
| 19 | (R) | 9 min. 45 sec. |

EXAMPLES 20–37

These examples illustrate the behaviour of compounds of formula (I) as vulcanization accelerators in combination with N-cyclohexyl-2-mercapto-benzothiazole sulfenamide (CBS).

Natural rubber based compounds were prepared, whose components are reported in Table 3.

TABLE 3

| Components | % by weight* |
|---|---|
| Natural rubber SMR 10 | 100.00 |
| Zinc oxide | 5.00 |
| Stearine | 1.00 |
| High-aromatics oil | 5.00 |
| Black N 375 | 45.00 |
| Sulfur | 2.00 |
| CBS | 1.00 |
| Compound of formula (I)** | 0.50 |

*% by weight, based on rubber.
**Compounds Nos. 1–13 and commercial enamines (ex Aldrich).

The Monsanto Rheometer is used under the following operating conditions:
oscillating arc: ±1°;
temperature: 150° C.

From the resulting rheometric curves, reported in FIGS. 2, 3 and 8, the $t_c(90)$ values were computed, and are reported in Table 4. The rheometric curves reported in FIGS. 2, 3 and 8 display the effectiveness as vulcanization accelerators, of the compounds having general formula (I) in combination with sulfenamide (CBS). Such an effectiveness is also demonstrated by the $t_c(90)$ values reported in Table 4, in which the vulcanization time $t_c(90)$ decreases from a value of 10 minutes down to a vulcanization time comprised within the range of from about 8 to 4 minutes.

In FIG. 2, the letters reported on the rheometric curves indicate the following compounds of formula (I):
Example 20: (F) CBS, as the only accelerator;
Example 23: (G) 1-morpholino-1-cyclopentene (ex Aldrich);
Example 22: (E) 1-pyrrolidino-1-cyclohexene (ex Aldrich);
Example 24: (H) 1-pyrrolidino-1-cyclopentene (ex Aldrich);
Example 26: (C) N-n-octen-($\Delta^1$)-yl piperidine (Compound No. 2);

In FIG. 3, the letters shown beside the rheometric curves indicate the following compounds of formula (I):
Example 20: (F) CBS, as the only accelerator;
Example 31: (I) N-n-octen-($\Delta^1$)-yl morpholine (Compound No. 7);
Example 32: (L) N-n-hexen-($\Delta^1$)-yl morpholine (Compound No. 8);
Example 33: (M) 1-dibutylamino-1-heptene (Compound No. 9);
Example 27: (A) N-n-hepten-($\Delta^1$)-yl pyrrolidine (Compound No. 3);
Example 25: (D) N-n-hexen-($\Delta^1$)-yl piperidine (Compound No. 1);

In FIG. 8, the letters reported on the rheometric curves indicate the following compounds of formula (I):
Example 20: (F) CBS, as the only accelerator
Example 34: (N) (Compound No. 10)

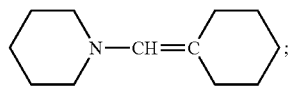

Example 35: (O) (Compound No. 11)

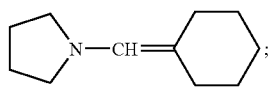

Example 36: (P) N-methyl-N-n-hepten-($\Delta^1$)-yl aniline (Compound No. 12);
Example 37: (Q) 1-phenyl-1-N-pentamethylene-ethylene (Compound No. 13);

TABLE 4

| Example No. | Enamine | $t_c(90)$ |
|---|---|---|
| 20 | none | 10 min. 00 sec. |
| 21 | 1-morpholino-1-cyclohexene | 7 min. 00 sec. |
| 22 | 1-pyrrolidino-1-cyclohexene | 5 min. 00 sec. |
| 23 | 1-morpholino-1-cyclopentene | 6 min. 00 sec. |
| 24 | 1-pyrrolidino-1-cyclopentene | 4 min. 15 sec. |
| 25 | Compound No. 1 | 4 min. 30 sec. |
| 26 | Compound No. 2 | 4 min. 30 sec. |
| 27 | Compound No. 3 | 4 min. 00 sec. |
| 28 | Compound No. 4 | 5 min. 48 sec. |
| 29 | Compound No. 5 | 4 min. 48 sec. |
| 30 | Compound No. 6 | 5 min. 36 sec. |
| 31 | Compound No. 7 | 6 min. 00 sec. |
| 32 | Compound No. 8 | 6 min. 00 sec. |
| 33 | Compound No. 9 | 4 min. 40 sec. |
| 34 | Compound No. 10 | 7 min. 25 sec. |
| 35 | Compound No. 11 | 6 min. 10 sec. |
| 36 | Compound No. 12 | 8 min. 20 sec. |
| 37 | Compound No. 13 | 5 min. 55 sec. |

EXAMPLE 38

114.19 g (1 mol) of heptaldehyde, 150 g of xylene and 12.5 g (corresponding to 0.127 mol in the solution of HCl at 100%) of hydrochloric acid (solution at 37%) are charged to a reactor of 500 ml of capacity equipped with mechanical stirrer, thermometer and reflux condenser with water separator.

The resulting mixture is kept with stirring and reflux d (100° C.) for 3 hours.

By using an apparatus for azeotropic distillation, 12 g is separated of acidic water (i.e., containing HCl) partially deriving from the hydrochloric acid solution and partially from the reaction, whilst xylene is recycled to the reactor.

During the heating and acidic water separation step, the reflux temperature increases from 100° C. up to 143° C.–145° C.

An amount of 46.6 g (0.5 mol) of aniline is then added during a 6-hours time with the reaction mixture being always kept at reflux temperature. During aniline addition, the boiling temperature of the reaction mixture increases from 143° C. up to 165° C., and about 16 g of acidic water is distilled off.

The reaction is completed by keeping the reaction mixture heated at a temperature of 165° C. during 1 hour after aniline addition.

To the so obtained mixture, cooled down to 90° C., 8.4 g (0.063 mol) of a solution of sodium hydroxide at 30% and 85 g of water are added, in order to neutralize the acidity of the mixture. The water phase is then separated, and the organic phase is washed with water. The organic phase is distilled by operating up to a temperature of 200° C. under atmospheric pressure in order to recover the solvent and then under a pressure of 10 mmHg in order to remove any residual aniline.

The resulting residue so obtained in the reactor, constituted by 125 g of a brown liquid material containing about 45% of product of formula (III), is submitted to a further vacuum distillation under a lower pressure than 1.0 mmHg, and at a temperature comprised within the range of from 170° C. to 230° C.

Such a distillation is carried out on a still constituted by a kettle of 250 ml of capacity equipped with thermometer, stirrer, 10 cm-long empty column, condenser and device for fractions collection. The central distillation fraction, which contains 85% of product of formula (III), is collected under the following conditions:
vacuum: 0.1 mmHg;
head temperature: 175° C.–180° C.;
kettle temperature: 190° C.–195° C.

EXAMPLE 39

Compounds based on styrene-butadiene rubber (SBR) were prepared according to ASTM D 3185-75, the components of which are reported in Table 5.

TABLE 5

| Components | % by weight* |
|---|---|
| SBR | 100.00 |
| Zinc oxide | 3.00 |
| Sulfur | 1.75 |
| Stearic acid | 1.00 |
| Black N 375 | 50.00 |
| N-t-butyl-2-benzothiazole sulfenamide | 1.00 |
| Mixture containing variable levels of compound of formula (III)** | 0.10 |

*% by weight based on styrene-butadiene rubber (SBR).
**% levels of compound of formula (III) in the blends: 8.2%; 26.0%; 46.6%; 84.6%.

Monsanto Rheometer 100 is used under the following operating conditions:
oscillating arc: ±1°;
temperature: 160° C.

From the resulting rheometric curves, reported in FIG. 6, the $t_c(90)$ values were computed. The resulting values are reported in Table 6.

TABLE 6

| Compound (III) concentration % | $t_c(90)$ |
|---|---|
| 0 | 18 min. 15 sec. |
| 8.2 | 16 min. 45 sec. |
| 26.0 | 16 min. 15 sec. |
| 46.6 | 15 min. 00 sec. |
| 84.6 | 13 min. 05 sec. |

From the data reported in Table 6, one will observe that the higher the percent level of compound of formula (III) in the blend, the shorter the required time to reach 90% of cross-linking maximum, it being thus confirmed that such a compound displays activity as vulcanization accelerator.

The invention claimed is:

1. A method of accelerating the vulcanization of rubber, comprising:
adding to a rubber an enamine of formula (II) as a vulcanization accelerator to form a mixture:

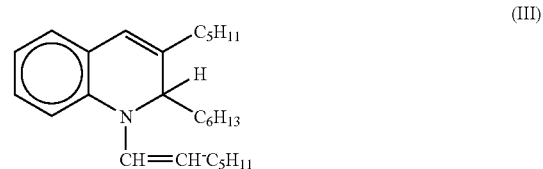

wherein said rubber vulcanizes faster with said enamine than without said enamine.

2. The method of claim 1, wherein said rubber is a synthetic rubber.

3. The method of claim 1, wherein said rubber is a natural rubber.

4. The method of claim 1, wherein said rubber is a synthetic rubber selected from the group consisting of SBR, NBR, BR and EPDM.

5. The method of claim 1, wherein said enamine is the only vulcanization accelerator.

6. The method of claim 1, wherein said mixture further comprises a second vulcanization accelerator.

7. The method of claim 6, wherein said second vulcanization accelerator is a mercaptobenzothiazole sulfonamide.

* * * * *